United States Patent
McIntyre et al.

(10) Patent No.: US 11,565,120 B2
(45) Date of Patent: Jan. 31, 2023

(54) DEFIBRILLATOR ACTIVATION AND STATUS INDICATION

(71) Applicant: HeartSine Technologies Limited, Belfast (GB)

(72) Inventors: Allister McIntyre, Newtownards (GB); Johnny Anderson, Holywood (GB)

(73) Assignee: HeartSine Technologies Limited, Belfast (GB)

( * ) Notice: Subject to any disclaimer, the term of this patent is extended or adjusted under 35 U.S.C. 154(b) by 343 days.

(21) Appl. No.: 16/219,377

(22) Filed: Dec. 13, 2018

(65) Prior Publication Data
US 2019/0192869 A1 Jun. 27, 2019

(30) Foreign Application Priority Data
Dec. 22, 2017 (GB) .................................. 1721767

(51) Int. Cl.
*A61N 1/39* (2006.01)
*A61N 1/04* (2006.01)

(52) U.S. Cl.
CPC ......... *A61N 1/3925* (2013.01); *A61N 1/3904* (2017.08); *A61N 1/3993* (2013.01); *A61N 1/046* (2013.01); *A61N 1/3968* (2013.01)

(58) Field of Classification Search
CPC ...... A61N 1/39; A61N 1/3904; A61N 1/3925; A61N 1/3993; A61N 1/02; A61N 1/025; A61N 1/046
USPC ................................................. 607/5–8
See application file for complete search history.

(56) References Cited

U.S. PATENT DOCUMENTS

| | | | | |
|---|---|---|---|---|
| 5,676,678 A | * | 10/1997 | Schad | A61B 17/29 606/170 |
| 6,871,094 B1 | * | 3/2005 | Allen | A61N 1/3925 600/518 |
| 9,349,303 B2 | * | 5/2016 | Freeman | G09B 23/288 |
| 10,926,099 B2 | * | 2/2021 | Aoyama | A61N 1/3968 |
| 2003/0208237 A1 | * | 11/2003 | Locke | A61N 1/3993 607/5 |
| 2003/0216785 A1 | * | 11/2003 | Edwards | A61N 1/3993 607/5 |
| 2013/0304142 A1 | * | 11/2013 | Curtin | A61N 1/3993 607/5 |
| 2016/0148495 A1 | * | 5/2016 | Buchanan | A61N 1/3904 340/539.17 |
| 2018/0169426 A1 | * | 6/2018 | Montague | G16H 80/00 |

* cited by examiner

*Primary Examiner* — Ahmed M Farah

(57) ABSTRACT

A defibrillator is provided comprising an activation mechanism having an activator and a status indicator, wherein the activator is disposable in a first condition in which the defibrillator is deactivated and in a second condition in which the defibrillator is activated and the status indicator is operable in at least a first mode in which a 'defibrillator ready' status of the defibrillator is indicated and a second mode in which a 'defibrillator not ready' status of the defibrillator is indicated. By having an activation mechanism which includes the activator and the status indicator, users of the defibrillator are not confused between separate activation and status indication devices and are able to use the activator promptly.

14 Claims, 2 Drawing Sheets

DEFIBRILLATOR ACTIVATION AND STATUS INDICATION

PRIORITY INFORMATION

The present application claims priority to United Kingdom application No. 1721767.0, filed 22 Dec. 2017, the content of which is incorporated herein by reference in its entirety.

BACKGROUND OF THE INVENTION

1. Field of the Invention

The disclosure relates to an activation mechanism for a defibrillator comprising a status indicator, which allows a user to more readily locate the activation mechanism and at the same time determine the defibrillator status.

2. Introduction

In instances of sudden cardiac arrest, prompt intervention using a defibrillator may have a positive outcome. Defibrillators, particularly automatic external defibrillators (AEDs), are therefore commonly found in many locations. Generally, defibrillators have an activation mechanism and a separate status indicator to indicate the condition of the defibrillator to a potential user or tester, for example 'ready to use' or 'not ready to use, etc. The status indicator can be periodically operative for a short period of time and inoperative for the rest of the time. When the defibrillator is to be used, it is important that it is activated as quickly as possible. The status indicator may confuse a user when trying to activate the defibrillator and particularly may be mistaken for the activation mechanism.

SUMMARY

Additional features and advantages of the disclosure will be set forth in the description which follows, and in part will be obvious from the description, or may be learned by practice of the disclosure. The features and advantages of the disclosure may be realized and obtained by means of the instruments and combinations particularly pointed out in the appended claims. These and other features of the present disclosure will become more fully apparent from the following description and appended claims, or may be learned by the practice of the disclosure as set forth herein.

According to the disclosure there is provided a defibrillator including an activation mechanism having an activator and a status indicator wherein the activator is disposable in a first condition in which the defibrillator is deactivated and in a second condition in which the defibrillator is activated and the status indicator is operable in at least a first mode in which a 'defibrillator ready' status of the defibrillator is indicated and a second mode in which a 'defibrillator not ready' status of the defibrillator is indicated.

BRIEF DESCRIPTION OF THE DRAWINGS

In order to describe the manner in which the above-recited and other advantages and features of the disclosure can be obtained, a more particular description of the disclosure briefly described above will be rendered by reference to specific embodiments thereof which are illustrated in the appended drawings. Understanding that these drawings depict only exemplary embodiments of the disclosure and are not therefore to be considered to be limiting of its scope, the disclosure will be described and explained with additional specificity and detail through the use of the accompanying drawings in which.

DETAILED DESCRIPTION

Figure 1:
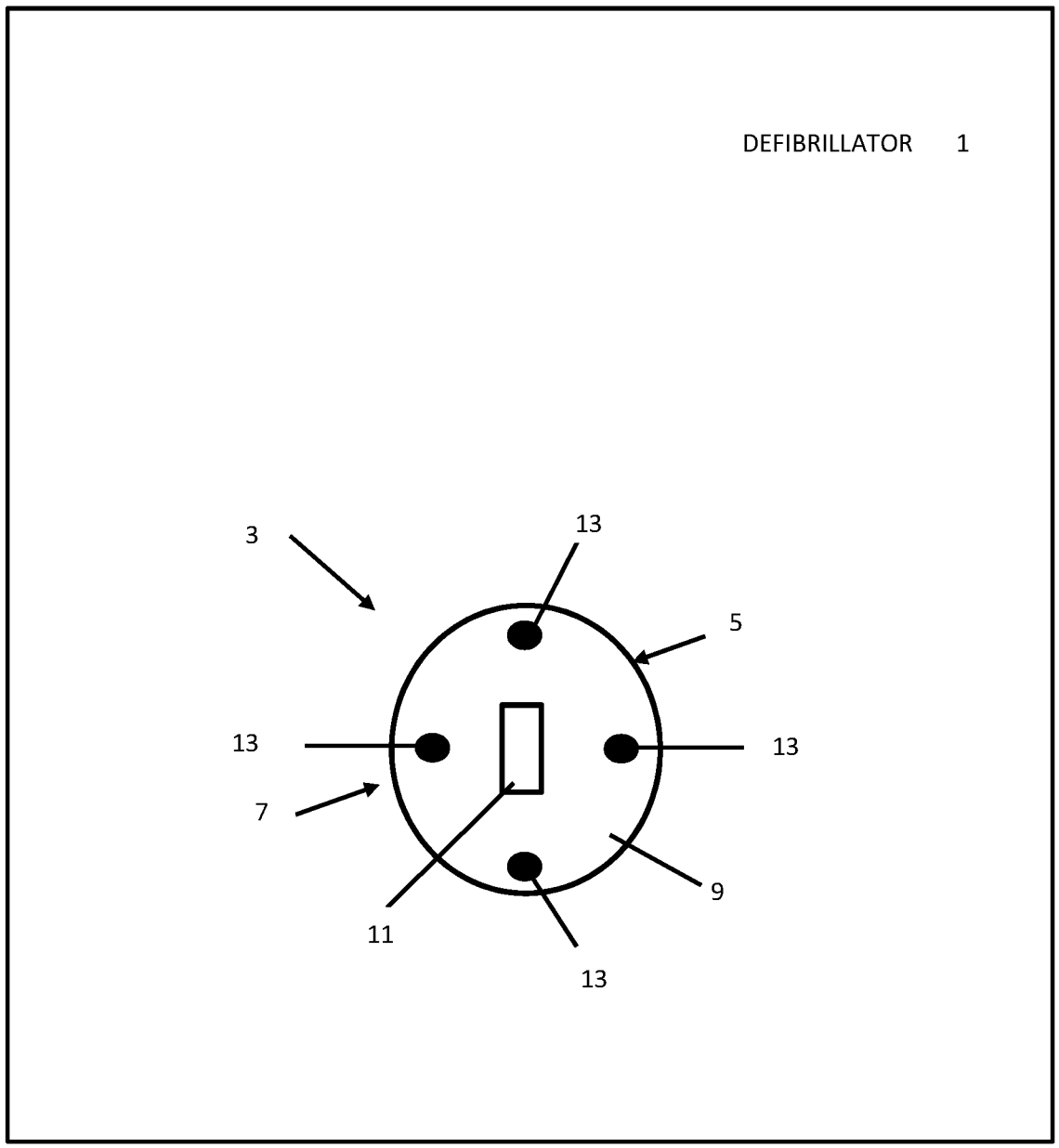
FIG. 1 is a schematic representation of a defibrillator comprising a first embodiment of an activation mechanism according to the disclosure.

This disclosure first provides a general description of a defibrillator that addresses the issues outlined above, and then shall describe an example defibrillator as shown in the figures. An example defibrillator includes an activation mechanism having an activator and a status indicator wherein the activator is disposable in a first condition in which the defibrillator is deactivated and in a second condition in which the defibrillator is activated and the status indicator is operable in at least a first mode in which a 'defibrillator ready' status of the defibrillator is indicated and a second mode in which a 'defibrillator not ready' status of the defibrillator is indicated.

By having an activation mechanism which includes the activator and the status indicator, users of the defibrillator are not confused between separate activation and status indication devices and are able to use the activator promptly.

The status indicator can include one or more lights. The one or more lights of the status indicator may be provided on an outer surface of the activation mechanism. The one or more lights of the status indicator may be contained within the activation mechanism to provide back lighting of an outer surface of the mechanism. The one or more lights of the status indicator may be arranged in an approximately circular shape. The one or more lights of the status indicator may be arranged in an approximately diamond shape. The one or more lights can include one or more light emitting diodes (LEDs) or some other visual indicator.

The one or more lights of the status indicator may be illuminated in the first mode in which the 'defibrillator ready' status of the defibrillator is indicated. The one or more lights of the status indicator may be unilluminated in the second mode in which the 'defibrillator not ready' status of the defibrillator is indicated. The one or more lights of the status indicator may be illuminated a first colour in the first mode in which the 'defibrillator ready' status of the defibrillator is indicated. The one or more lights of the status indicator may be illuminated a second colour in the second mode in which the 'defibrillator not ready' status of the defibrillator is indicated. The first colour may be green. The second colour may be red, in one non-limiting example.

In either the first mode or the second mode of the defibrillator or both the first mode and the second mode of the defibrillator, the one or more lights of the status indicator may be illuminated in an illumination pattern. The illumination pattern can include continued illumination of the one or more lights of the status indicator for a pre-determined period of time. The illumination pattern can include repeated flashing of the one or more lights of the status indicator. The illumination pattern can include repeated increasing of the illumination of the one or more lights of the status indicator from a minimum illumination to a maximum illumination and decreasing of the illumination of the one or more lights of the status indicator from the maximum illumination to the minimum illumination. The illumination pattern may include repeated increasing of the illumination of the one or more lights of the status indicator from a minimum illumination to a maximum illumination at a first speed and decreasing of the illumination of the one or more lights of the status indicator from the maximum illumination to the minimum illumination at a second, slower, speed.

The activator can include a wireless signal receiver and be disposable in the first condition and the second condition on receiving instructions from a wireless signal transmitter. The wireless signal transmitter may be any of a smart card, a key fob.

The activator can include a voice-activated unit and be disposable in the first condition and the second condition on receiving voice instructions. The activator can include a touch screen and be disposable in the first condition and the second condition on receiving instructions from the touch screen.

The activator may be disposable in the first condition and the second condition by being movable between a first position in which the defibrillator is deactivated and a second position in which the defibrillator is activated. The activator may be movable between the first position and the second position by a user of the defibrillator. The activator can include any of a button, a hook, a dial, a slider, a handle, a knob, a key, a switch. In a preferred embodiment, the activator includes a button which is movable between the first position and the second position by pressing. The button may automatically release from the second position.

The activator can include a sign which indicates the activator to a user of the defibrillator. The sign may be any of rectangular, circular, oval, square. The sign may be positioned substantially centrally in the activator. The sign may be positioned on an outer surface of the activator.

The activator can include one or more lights to illuminate the activator. The one or more lights of the activator may illuminate the sign of the activator. This may be used to indicate the activator to a user of the defibrillator. The one or more lights of the activator may be contained within the activation mechanism to provide back lighting of the sign of the activator. The one or more lights of the activator may be provided on an outer surface of the activation mechanism to illuminate the sign of the activator. The one or more lights of the activator can include one or more LEDs. The one or more lights of the activator can include the one or more lights of the status indicator.

The one or more lights of the activator may be illuminated in an illumination pattern. The illumination pattern can include continued illumination of the one or more lights of the activator for a pre-determined period of time. The illumination pattern can include repeated flashing of the one or more lights of the activator. The illumination pattern can include repeated increasing of the illumination of the one or more lights of the activator from a minimum illumination to a maximum illumination and decreasing of the illumination of the one or more lights of the activator from the maximum illumination to the minimum illumination. The illumination pattern can include repeated increasing of the illumination of the one or more lights of the activator from a minimum illumination to a maximum illumination at a first speed and decreasing of the illumination of the one or more lights of the activator from the maximum illumination to the minimum illumination at a second, slower, speed.

Having introduced the concepts disclosed herein, the disclosure now turns to the figures. Referring to FIG. 1, a defibrillator 1 includes an activation mechanism 3. The activation mechanism 3 includes an activator 5 and a status indicator 7. It will be appreciated that the defibrillator includes other components such as electrodes, defibrillation shock circuitry, etc. which are not shown.

The activator 5 includes a button 9 and a sign 11 disposed on an outer surface of the button 9 of the activator 5. The activator 5 further includes a single, elongate light (not shown). The light is contained within the activator 5 at a substantially central position of the button 9, to provide back lighting of the sign 11 on the outer surface of the button 9 of the activator 5. In this embodiment, the light uses an illumination pattern comprising repeated increasing of the illumination of the light from a minimum illumination to a maximum illumination and decreasing of the illumination of the light from the maximum illumination to the minimum illumination. It will be appreciated that other illumination patterns may be used. The illuminated sign 11 indicates the button 9 of the activator 5 to a user of the defibrillator 1, so that the user can easily distinguish the activator 5 from other controls of the defibrillator 1.

The status indicator 7 includes four lights 13 provided on an outer surface of the activation mechanism 3 and arranged in an approximately diamond shape, as shown. Other shapes, such as circular or square, for example, are contemplated as well. The lights 13 are illuminated green in the first mode of the status indication device 7 which indicates the 'defibrillator ready' status of the defibrillator 1. The lights 13 are illuminated red in a second mode of the status indication device 7 which indicates the 'defibrillator not ready' status of the defibrillator 1. In this embodiment, the lights 13 are illuminated and remain illuminated for a pre-determined period of time. It will be appreciated that other illumination patterns may be used.

When a user needs to use the defibrillator 1, they first check if the lights 13 of the status indicator 7 are green. If this is the case, the user presses the button 9 of the activator 5. This causes the button 9 of the activator 5 to be disposed in the second condition in which the defibrillator 1 is activated.

As the activation mechanism 3 includes the activator 5 and the status indicator 7, the user is not confused by a separate status indication device, mistaking this for an activation device, and is able to use the activator 5 of the activation mechanism 3 promptly.

Figure 2:
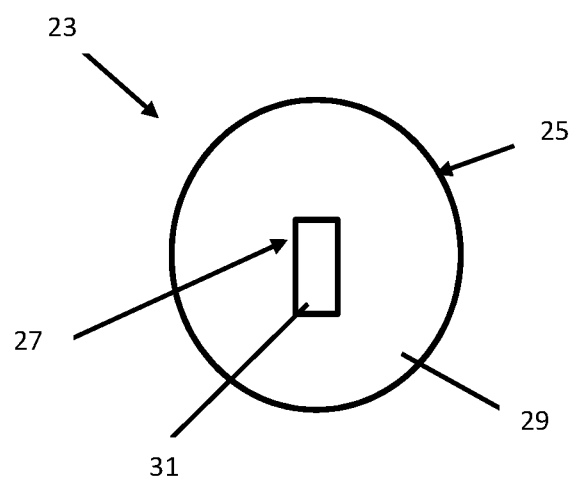
FIG. 2 is a schematic representation of a defibrillator comprising a second embodiment of an activation mechanism according to the disclosure.

Referring to FIG. 2, a defibrillator 21 includes an activation mechanism 23. The activation mechanism 23 includes an activator 25 and a status indicator 27. It will be appreciated that the defibrillator includes other components such as electrodes, defibrillation shock circuitry, etc. which are not shown.

The activator 25 includes a button 29 and a sign 31 disposed on an outer surface of the button 29 of the activator 25. The status indicator 27 includes a single, elongate light (not shown). The light is contained within the activator 25 at a substantially central position of the button 29, to provide back lighting of the sign 31 on the outer surface of the button 29 of the activator 25. The light of the status indicator 27 is illuminated green in the first mode of the status indication device 27 which indicates the 'defibrillator ready' status of the defibrillator 21. The light of the status indicator 27 is illuminated red in a second mode of the status indication device 7 which indicates the 'defibrillator not ready' status of the defibrillator 21. In this embodiment, the light of the status indicator 27 is illuminated and remain illuminated for a pre-determined period of time. It will be appreciated that other illumination patterns may be used. The illuminated sign 11 indicates the button 9 of the activator 5 to a user of the defibrillator 1, so that the user can easily distinguish the activator 5 from other controls of the defibrillator 1. The illuminated sign 11 also indicates the status of the defibrillator 21 to the user.

When a user needs to use the defibrillator 21, they first check if the light of the status indicator 27, which back lights the sign 31, is green. If this is the case, the user presses the button 29 of the activator 25. This causes the button 29 of the activator 25 to be disposed in the second condition in which the defibrillator 1 is activated.

As the activation mechanism 23 includes the activator 25 and the status indicator 27, the user is not confused by a separate status indication device, mistaking this for an activation device, and is able to use the activator 25 of the activation mechanism 23 promptly.

Whether to practice a method or in connection with the defibrillator embodiment, where necessary, computer components are included within the scope of this disclosure. Such components can include, without limitation, a processor, a bus that communicates data between computer components, an input component, an output component, graphical user interfaces, speech processing or speech related components, multi-modal input components, various modules which include computer code programmed to cause the processor to perform certain functions as disclosed herein, or non-transitory computer-readable devices that store computer code or computer-implemented instructions, which, when implemented, cause a processor or a specific module to perform certain operations.

We claim:

1. A defibrillator comprising:
an activation mechanism having an activator and a status indicator, wherein the status indicator comprises one or more lights that are illuminated in an illumination pattern in which the illumination pattern comprises continued illumination of the one or more lights for a pre-determined period of time, and wherein the activator is set in a first condition in which the defibrillator is deactivated and set in a second condition in which the defibrillator is activated and the status indicator is operable in at least a first mode in which a 'defibrillator ready' status of the defibrillator is indicated and a second mode in which a 'defibrillator not ready' status of the defibrillator is indicated.

2. A defibrillator according to claim 1, in which the one or more lights of the status indicator are illuminated a first colour in the first mode in which the 'defibrillator ready' status of the defibrillator is indicated and are illuminated a second colour in the second mode in which the 'defibrillator not ready' status of the defibrillator is indicated.

3. A defibrillator according to claim 1, in which, in either the first mode or the second mode of the defibrillator, the one or more lights of the status indicator are illuminated in the illumination pattern.

4. A defibrillator according to claim 1, in which the activator is set in the first condition and set the second condition by being movable between a first position in which the defibrillator is deactivated and a second position in which the defibrillator is activated.

5. A defibrillator according to claim 4 in which the activator comprises any of a button, a hook, a dial, a slider, a handle, a knob, a key, a switch.

6. A defibrillator according to claim 1, in which the activator comprises a sign which indicates the activator to a user of the defibrillator.

7. A defibrillator according to claim 6, in which the activator comprises one or more lights which illuminate the sign of the activator.

8. A defibrillator according to claim 1, in which the one or more lights are contained within the activation mechanism.

9. A defibrillator according to claim 8, wherein the one or more lights being contained within the activation mechanism provides a back lighting of an outer surface of the defibrillator.

10. A defibrillator according to claim 1, in which the one or more lights are provided on an outer surface of the activation mechanism.

11. A defibrillator according to claim 1, in which the illumination pattern comprises repeated flashing of the one or more lights.

12. A defibrillator according to claim 1, in which the illumination pattern comprises repeated increasing of the illumination of the one or more lights from a minimum illumination to a maximum illumination and decreasing of the illumination of the one or more lights from the maximum illumination to the minimum illumination.

13. A defibrillator according to claim 1, in which the illumination pattern comprises repeated increasing of the illumination of the one or more lights from a minimum illumination to a maximum illumination at a first speed and decreasing of the illumination of the one or more lights from the maximum illumination to the minimum illumination at a second, slower, speed.

14. A defibrillator according to claim 1, wherein the status indicator comprises one or more lights contained within the activation mechanism that provide a back lighting of an outer surface of the activation mechanism.

* * * * *